US009693848B2

(12) United States Patent
Dunlop

(10) Patent No.: US 9,693,848 B2
(45) Date of Patent: Jul. 4, 2017

(54) APPARATUS AND METHOD FOR MAINTAINING PATIENT TEMPERATURE DURING A PROCEDURE

(71) Applicant: Colin Dunlop, East Ryde (AU)

(72) Inventor: Colin Dunlop, East Ryde (AU)

( * ) Notice: Subject to any disclaimer, the term of this patent is extended or adjusted under 35 U.S.C. 154(b) by 370 days.

(21) Appl. No.: 14/213,615

(22) Filed: Mar. 14, 2014

(65) Prior Publication Data

US 2015/0020803 A1 Jan. 22, 2015

Related U.S. Application Data

(63) Continuation of application No. PCT/AU2012/001103, filed on Sep. 14, 2012.

(51) Int. Cl.
*A61M 11/00* (2006.01)
*A61D 7/04* (2006.01)
(Continued)

(52) U.S. Cl.
CPC ............... *A61D 7/04* (2013.01); *A61D 99/00* (2013.01); *A61M 16/01* (2013.01); *A61M 16/0875* (2013.01); *A61M 16/0891* (2014.02); *A61M 16/1075* (2013.01); *A61M 16/1095* (2014.02); *A61M 16/0816* (2013.01);
(Continued)

(58) Field of Classification Search
CPC ..... A61D 7/04; A61D 99/00; A61M 16/0875; A61M 16/1095; A61M 16/0891; A61M 16/1075; A61M 16/01; A61M 2205/3653; A61M 16/0816; A61M 16/22; A61M 2230/50; A61M 2205/3368; A61M 2202/0208; A61M 2205/502; A61M 16/18
See application file for complete search history.

(56) References Cited

U.S. PATENT DOCUMENTS 4,967,744 A 11/1990 Chua
6,078,730 A * 6/2000 Huddart ................ A61M 16/08
219/536
(Continued)

FOREIGN PATENT DOCUMENTS

AU 2012/308102 5/2013
EP 1352670 A1 10/2003
(Continued)

OTHER PUBLICATIONS

Examination Report issued May 9, 2014 by the Australian Patent Office for AU 2013/204262 filed on Apr. 12, 2013 (1st Named Inventor—Dunlop) (3 pages).
(Continued)

*Primary Examiner* — Steven Douglas
(74) *Attorney, Agent, or Firm* — Ballard Spahr LLP

(57) ABSTRACT

An apparatus and method for maintaining patient temperature during an anaesthetic procedure. Patients, particularly small patients, can lose body temperature when undergoing surgery or other procedures where they are anaesthetized. The process of breathing the cool anaesthetic gas contributes to the temperature loss of the patient. An anaesthetic apparatus is arranged to warm the gas being provided for the patient to breathe, to facilitate maintaining body temperature. An inspired limb of an anaesthetic circuit comprises tubing with a heating conductor for heating the inspired gas.

18 Claims, 14 Drawing Sheets

(51) Int. Cl.
    *A61M 16/01*      (2006.01)
    *A61M 16/10*      (2006.01)
    *A61D 99/00*      (2006.01)
    *A61M 16/08*      (2006.01)
    *A61M 16/18*      (2006.01)
    *A61M 16/22*      (2006.01)

(52) U.S. Cl.
    CPC .............. *A61M 16/18* (2013.01); *A61M 16/22* (2013.01); *A61M 2202/0208* (2013.01); *A61M 2205/3368* (2013.01); *A61M 2205/3653* (2013.01); *A61M 2205/502* (2013.01); *A61M 2230/50* (2013.01)

(56) References Cited

U.S. PATENT DOCUMENTS

| | | |
|---|---|---|
| 7,396,995 B2 | 7/2008 | Laurent et al. |
| 2004/0102731 A1* | 5/2004 | Blackhurst ......... A61B 1/00154 604/26 |
| 2008/0105257 A1 | 5/2008 | Klasek et al. |
| 2009/0250055 A1 | 10/2009 | Radomski et al. |
| 2011/0023874 A1 | 2/2011 | Bath et al. |

FOREIGN PATENT DOCUMENTS

| | | |
|---|---|---|
| WO | WO 02/32486 | 4/2002 |
| WO | WO 2004/052250 | 6/2004 |
| WO | WO 2008/043155 | 4/2008 |
| WO | WO 2009/022004 | 2/2009 |
| WO | WO 2010/111750 | 10/2010 |
| WO | WO 2011/123902 | 10/2011 |
| WO | WO 2013/037004 A1 | 3/2013 |

OTHER PUBLICATIONS

Examination Report issued May 2, 2014 by the Australian Patent Office for AU 2013/204262 filed on Apr. 12, 2013 (1st Named Inventor—Dunlop) (3 pages).

International Search Report dated Oct. 24, 2012, issued in International Appl. No. PCT/AU2012/001103, filed on Sep. 14, 2012.

* cited by examiner

Assembly Instructions
• Connect controller to Hose and Heater Assembly

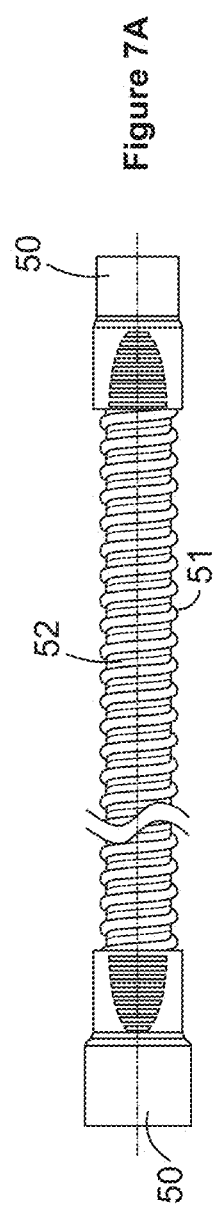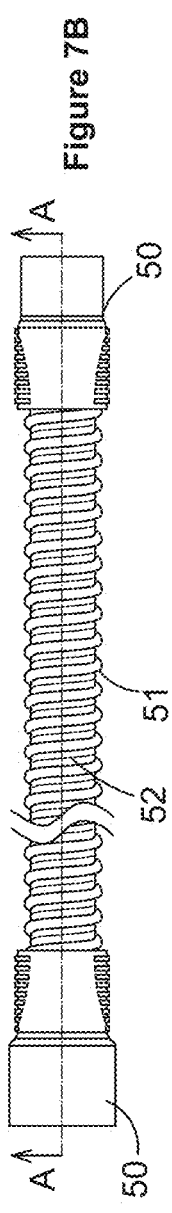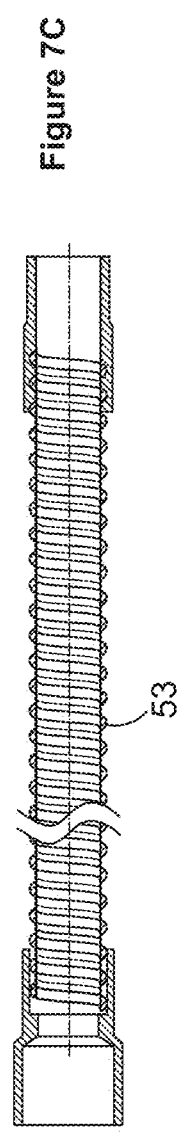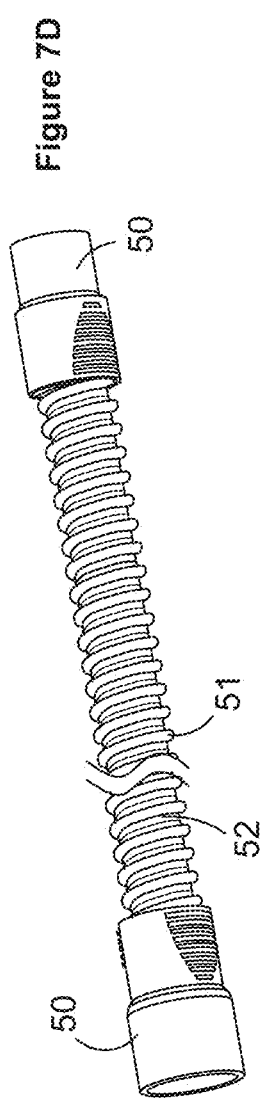

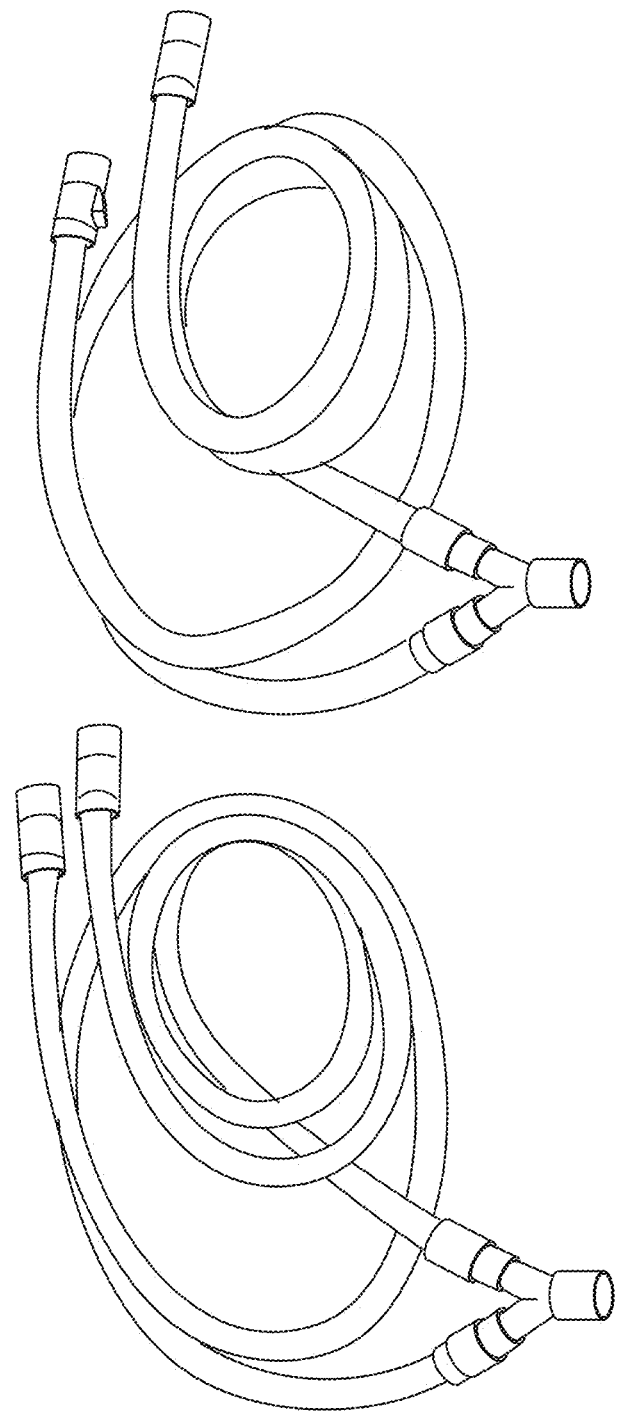

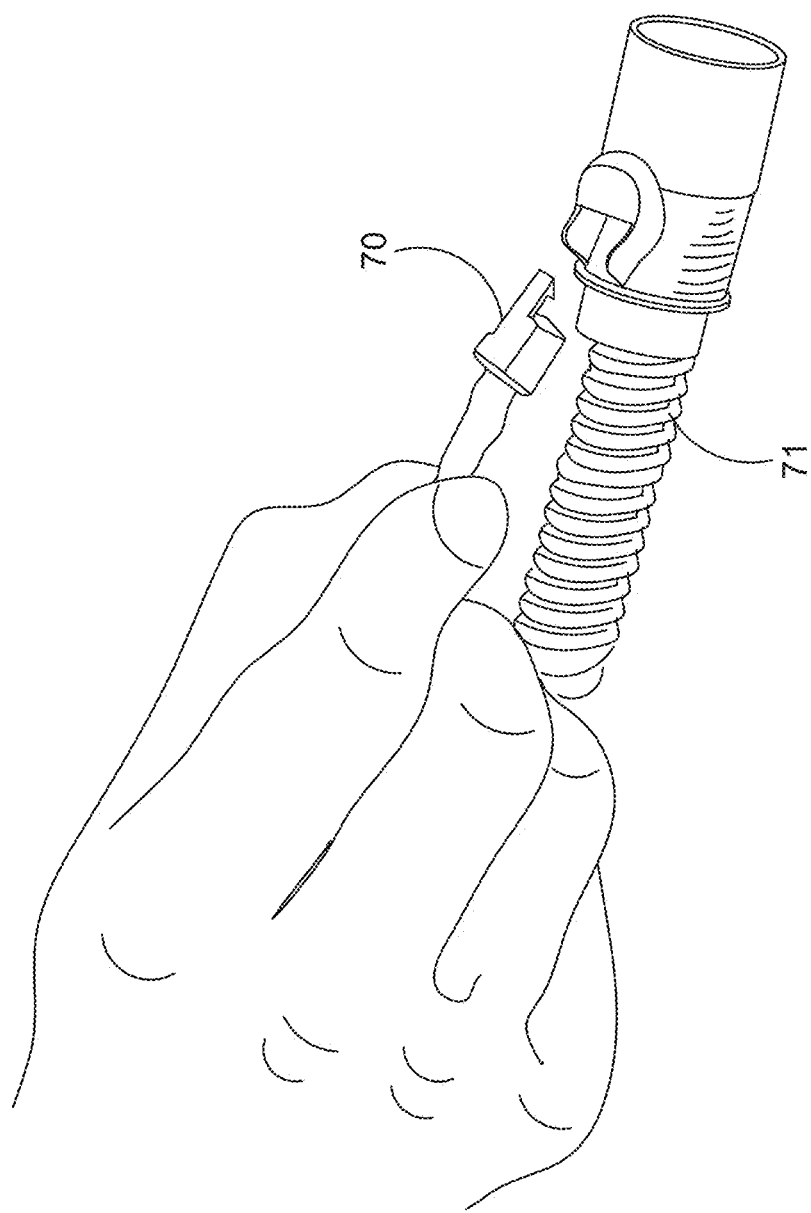

APPARATUS AND METHOD FOR MAINTAINING PATIENT TEMPERATURE DURING A PROCEDURE

CROSS-REFERENCE TO RELATED APPLICATIONS

This application is a continuation of International Application No. PCT/AU2012/001103 filed on Sep. 14, 2012, which claims priority to Australian Patent Application No. 2012903900 filed on Sep. 7, 2012 and to Australian Patent Application No. 2011903770 filed on Sep. 14, 2011, the disclosures of which are incorporated herein in their entirety by reference.

FIELD OF THE INVENTION

The present invention relates to an apparatus and method for maintaining patient temperature during a medical procedure and, particularly, but not exclusively, to a method and apparatus for maintaining patient temperature during anaesthesia.

BACKGROUND OF THE INVENTION

A problem with medical procedures such as, for example, surgery is maintenance of the temperature of the patient.

This is a particular problem for smaller patients, for example, less than 40 kgs. It has been found that for in the order of 85% of small animals (less than 40 kgs, but more particular less than 30 kgs and more particular less than 20 kgs), the body temperature drops below their normal body temperature during an anaesthetic procedure. There is therefore a significant danger of hypothermia, and consequent complications associated with this, including slow recovery time.

SUMMARY OF THE INVENTION

In accordance with a first aspect, the present invention provides an anaesthetic apparatus arranged for the delivery of anaesthesia to a patient, the apparatus comprising a conduit for delivering a gas including anaesthetic to a patient, the conduit comprising a heating arrangement arranged to heat the gas within the conduit.

Advantageously, in at least an embodiment, heating the gas facilitates maintenance of the temperature of the patient, as the patient breaths the heated gas.

The present Applicant's have found that, in conventional anaesthesia, where the gas is not heated, the process of breathing the anaesthetic gas (which is usually cool and dry) contributes to cooling of the patient leading to potential hypothermia. Embodiments of the present invention minimise this danger by heating the gas within the anaesthetic apparatus so that the patient is breathing heated gas.

The temperature to which the gas is heated will depend upon the type of patient. Animals under 40 kgs, small animals (30 kgs or less), depending on the usual body temperature and size of animal, the gas will be heated to between 30-50° C. in an embodiment to between 34-45° C. and in an embodiment between 35-38° C.

In an embodiment, the apparatus comprises an anaesthetic circuit, comprising at least an inspired limb (the part of the circuit through which gas is provided to the patient). In this embodiment, the inspired limb comprises the conduit. Gas on the way to the patient is therefore heated. The anaesthetic apparatus may also comprise an expired limb. This may or may not comprise a heated conduit.

In an embodiment, the anaesthetic apparatus comprises a re-breathing circuit (circle system). In an alternative embodiment, the anaesthetic apparatus may comprise a non-re-breathing circuit (open system).

In an embodiment, the conduit comprises tubing, comprising a tubing wall defining a passageway along which gas may pass. In an embodiment the internal surface of the tubing wall (adjacent the passageway) is smooth. This contrasts with typical tubing used in prior art anaesthetic circuits, which is corrugated. In an embodiment, the heating arrangement comprises a conductive element wound about the tubing wall. In an embodiment, the heating element is wound about the internal surface tubing adjacent the passageway. In an alternative embodiment, the element is wound within the tubing wall. In an embodiment, the tubing has ribs around the wall. In an embodiment, the heating element is wound around underneath or inside the ribs. In an embodiment, the heating element is a conductive wire. Electricity is passed through the wire to heat it.

The Applicant's have found that having smooth wall tubing facilities heating of the gas within the bore of the tubing. They have also found that the smooth wall facilitates flow of the gas along the passageway.

In an embodiment, the passageway of the tubing is between 10-18 mm in diameter. In an embodiment, it is between 12-16 mm. In one embodiment, the tubing has a bore of 12 mm.

In another embodiment, the tubing has a bore of 16 mm.

Conventional tubing used in an anaesthetic apparatus is in the order of 20-25 mm (usually 20-22 mm) in diameter. It has been previously thought that lower passageway diameters may lead to high resistance within the anaesthetic circuit leading to difficulty in the patient breathing. The Applicant's have found, surprisingly, that with smooth walled tubing, lesser diameters than 20 mm can be used without deleteriously increasing the resistance of the anaesthetic circuit and affecting patients breathing. Further, with lower diameter tubing, the Applicant's have found that the gas flowing within the passageway is heated more effectively.

In an embodiment, the anaesthetic apparatus comprises temperature controller, arranged to regulate the heating arrangement to maintain temperature of the gas at a predetermined level. In an embodiment, the apparatus further comprises a temperature monitor arranged to monitor the temperature of the gas. In an embodiment, the temperature sensor is positioned proximate the breathing orifice of the patient, in use, in order to measure the expired temperature. Where the apparatus comprises an anaesthetic circuit, the temperature sensor may be positioned in the expired limb of the circuit.

In an embodiment, the temperature controller may be arranged to receive an input indicative of the patient's actual temperature. A temperature sensor in the patient (e.g. rectal or oesophageal thermometer, or any other type of temperature sensor) may provide information on the patient's actual body temperature to the temperature controller. This can be used by the temperature controller to regulate the output of the heating arrangement. For example, if the patient is too warm, no heating may be provided by the heating arrangement. If the patient is too cold, heating may be increased.

In an embodiment, where there is a temperature monitor monitoring expired breath temperature or the temperature of the anaesthetic circuit, and a temperature monitor monitoring temperature of the animal, the differential temperature (between the animal and the circuit) can be monitored. This may allow a measurement of heat gained or lost as controlled by the anaesthetic apparatus. This can be particularly useful for research, for example, as well as having other uses.

In accordance with a second aspect, the present invention provides a method of maintaining the warmth of a patient during anaesthesia, comprising the step of delivering warmed gas to the patient during anaesthesia.

In an embodiment, the gas includes anaesthetic. In an embodiment, the step of delivering warmed gas comprises the step of heating the gas. In an embodiment, the step of heating the gas comprises the step of heating the gas in a conduit delivering the gas in an anaesthetic circuit. In an embodiment, the gas is delivered via the inspired limb of the anaesthetic circuit. The inspired limb includes or comprises the conduit.

In an embodiment, the gas may be heated by a heating arrangement such as described above in relation to the first aspect of the invention. In another embodiment, the gas may be heated by heating the conduit in another way. For example, the conduit may be placed in a warm water bath. The conduit would not necessarily need any heating elements in this case, the warm water bath would provide the heat to the inspired limb of the anaesthetic circuit, for example.

It is known to maintain the warmth of patients during surgery and anaesthesia by using patient warming blankets placed around, under or over the patient. See Applicant's earlier patent application numbers PCT/AU2003/001626, PCT/AU2007/001553, PCT/AU2010/000383 and PCT/AU2011/000410 the contents of which are incorporated herein by reference. In an embodiment, the conduit of an anaesthetic circuit may be placed proximate the blanket so that the blanket passes heat to the conduit. This would be another way of heating the gas in the conduit.

In accordance with a third aspect, the present invention provides an apparatus for maintaining patient warmth during a medical procedure, the apparatus comprising a conduit along which gas is passed for breathing by the patient, the conduit comprising a heating arrangement arranged to heat the gas within the conduit.

The apparatus may be used during a medical procedure or during recovery from a medical procedure. For example, to maintain the warmth of animals recovering in cages following an operation, a nitrogen/oxygen mixture may be provided along the heated conduit. Any other gas mixture may be provided.

In accordance with a fourth aspect, the present invention provides a method for maintaining patient warmth, comprising the steps of providing a gas for breathing by the patient, the gas being heated, whereby to maintain patient warmth.

In an embodiment, the gas is passed along a conduit to the patient, and is heated within the conduit.

BRIEF DESCRIPTION OF THE DRAWINGS

Features and advantages of the present invention will become apparent from the following description of embodiments thereof, by way of example only, with reference to the accompanying drawings, in which:

FIGS. 7A to 7D are various views of heated tubing used with an apparatus in accordance with an embodiment of the present invention;

FIGS. 9 and 10 are views of anaesthetic lines for an anaesthetic apparatus in accordance with embodiments of the present invention including heated tubing in accordance with embodiments of the present invention;

FIG. 11 is a view of heated tubing in accordance with an embodiment of the present invention, showing a connector for connecting a power supply to a heating element.

DETAILED DESCRIPTION OF EMBODIMENTS

Figure 1:
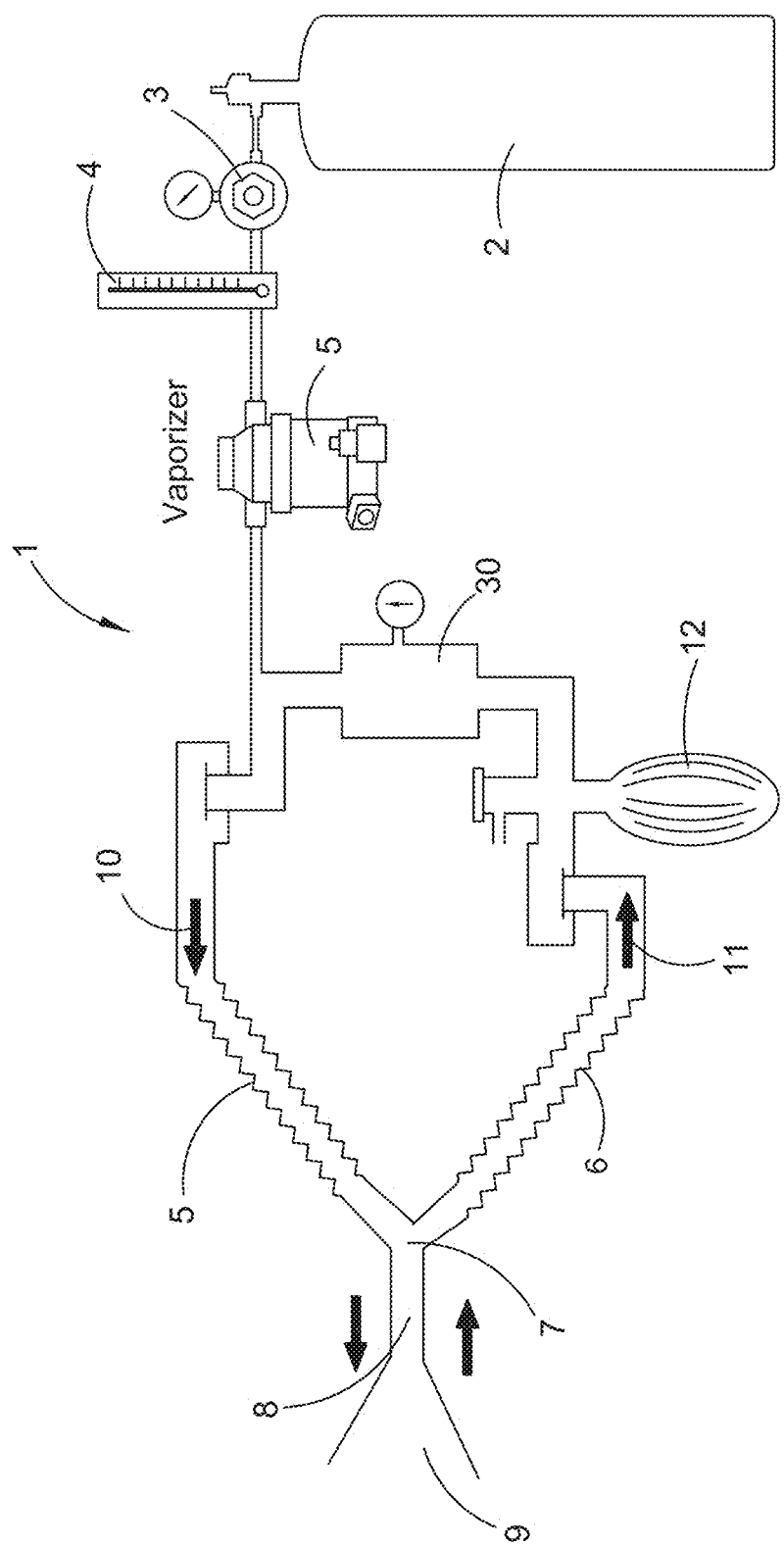
FIG. 1 is a diagram of a prior art anaesthetic circuit.

Referring to FIG. 1, a prior art anaesthetic circuit of the re-breathing type (circle type) is illustrated. The anaesthetic circuit is designated generally by reference numeral 1. The anaesthetic circuit 1 includes a means of providing oxygen, in this case being a gas cylinder 2 containing oxygen. A regulator 3 is provided to regulate the pressure of the oxygen supply and a flow meter 4 provides an indication of the gas flow. A vaporiser 5 is provided for introduction of anaesthetic (and perhaps additional gases) to the gas flow. The system includes anaesthesia lines 5 and 6, of standard corrugated tubing. The anaesthetic lines 5 and 6 form a 'Y' connection 7 with a 'Y' piece 7 and a distal opening 8 of a mask 9. The mask 9 is used to provide gas to the patient's mouth and/or nose. Other means for delivering gas to the patient's respiratory orifice, apart from a mask may be used, for example, the patient may be intubuted. Any other means be used.

Fresh gas flow comes down line 6 from the vaporiser 5 in the direction of arrow 10. Line 5 is the "inspired limb".

Exhaust gas flow travels up the other line 26 "expired limb", arrow 11. A reservoir bag 12 is connected to the distal end of the expired limb 6 and has an outlet which proceeds to a scrubber 30 which is arranged to remove carbon dioxide from the exhaust gas. The scrubbed gas re-enters the lines at the other side of the scrubber 30.

This is one type of circuit in which the patient re-breaths scrubbed air. It is the most popular circuit that is used for human anaesthesia, and is also used in veterinary anaesthesia. It is effective in reducing pollution and waste gases.

Other types of circuit include in the non-re-breathing circuit, where exhaled gases are not re-breathed, but instead scavenged. The supply of gas/anaesthetic is a continuous supply. Non-re-breathing circuits are generally used with smaller patients, such as small animals (less than 25 kgs), neonates and small infants.

A problem with traditional anaesthetic systems, whether a closed circuit re-breathing systems, or open circuit non-re-breathing systems, is that the patient tends to lose heat with every breath, because they are breathing cold, dry gas. For small animal patients (e.g. less than 30 kgs, even more so when less than 25 kgs even more so less than 20 kgs), hypothermia may occur in up to 85% of anaesthetised patients. The small animal patient's temperatures can commonly fall to between 30-34° C., which can result in dangerous hypothermia and poorer quality recoveries. Warming animals in recovery is slow, consumes a lot of nursing time and, if managed incorrectly, can result in thermal injuries e.g. being burnt by warming devices, such as hot water bottles or electrical heating pads. The Applicant's believe the prevention of heat loss in the first place is a more effective problem management strategy.

Heat loss or gain occurs in an exponential manner with its greatest impact on small patients. In part this is because of their large body surface area relative to body mass. Hypothermia occurs in anaesthetised cats, dogs and even young foals, during anaesthesia.

Further, anaesthesia depresses CNS thermo regulation and prevents the usual methods of conserving heat such as seeking warm environments, body positioning, hair coat direction and peripheral vasoconstriction all generating heat by shivering. Heat loss during surgery is exacerbated by clipping hair from surgery sites, using cold or evaporated skin prep solutions, wetting and flatting the hair coat, opening body cavities.

Problems with hypothermia include:
CNS depression which reduces the requirement for anaesthetic drugs so patients appear "deeper"
lower tissue blood flow alters drug distribution, metabolism and excretion, prolonging recovery
peripheral vasoconstriction decreases surface heating efficiency Preventing hypothermia during surgery traditionally relies on skin surface contact heating from hot water filled bottles, circulating warm water blankets and electric heating pads placed under the animal or under the surgery table top. IV fluid has been warmed by placing IV fluid lines in dishes of warm water.

Calories and Warming IV Fluids

A calorie (cal) is the amount of heat required to raise 1 ml (or 1 gm) of $H_2O$ 1° C. The specific heat of animal tissue is 0.83 cal/gm. Therefore a 10 kg dog requires 8,300 cal (8.3 kcal) to raise its temperature 1° C.

Warming IV Fluid Administered During Surgery

A 10 kg dog administered IV fluid at 10 ml/kg/hr=100 ml/hr. If the fluid is warmed to 44° C. and the dog is 34° C., then we can deliver:

(44−34° C.=) 10° C.×100 ml/hr=1000 cal/hr.

To warm the 10 kg at 34° C. dog to 37° C., the dog needs:

(37−34=) 3° C.×8,300 cal=25,000 cal (approx)/1000 cal/hr (from the IV fluid)=25 hours!

Warming IV fluid may prevent cold fluid exacerbating heat loss but is not effective for warming severely hypothermic animals.

Respiratory Heat Loss Due to Humidification is Significant

During inspiration the nose and pharyngeal mucosa transfer heat and moisture to the air which is largely recovered during expiration, thus conserving heat. Air has a low heat capacity (0.24 cal/gm) and a low weight (1.3 gm/l). Saturated air holds 44 mg H2O/L at 37° C. which requires 24 calories. A 10 kg dog taking 20×100 ml breaths/min ventilates 120 L/hr so requires (24 cal/L×120 L/hr)=2880 cal/hr for humidification. Intubation inhibits heat/moisture conservation via the nose, resulting in body temperature loss of about ⅓° C./hr.

Thermal Burns

Thermal injury to skin is an exponential relationship between source temperature and contact time. Burns do occur at temperatures below 50° C. and are still commonly seen. Hot tap water may reach 60° C. and 10 seconds of skin contact would result in epidermal necrosis. In 2008 the UK Veterinary Defence Society reported a high incidence of burns caused by use of warmed wheat bags which can produce similar temperatures.

Electric heating pads usually have a low thermal mass and cycle on until the thermostat reaches its high point, then cycle off until cooling to the low point, then turn back on repeating the process. Simple controllers can be variable in performance or fail, causing higher temperature delivery and potentially burns. These devices should always be insulated from the animal's skin surface.

Figure 2:
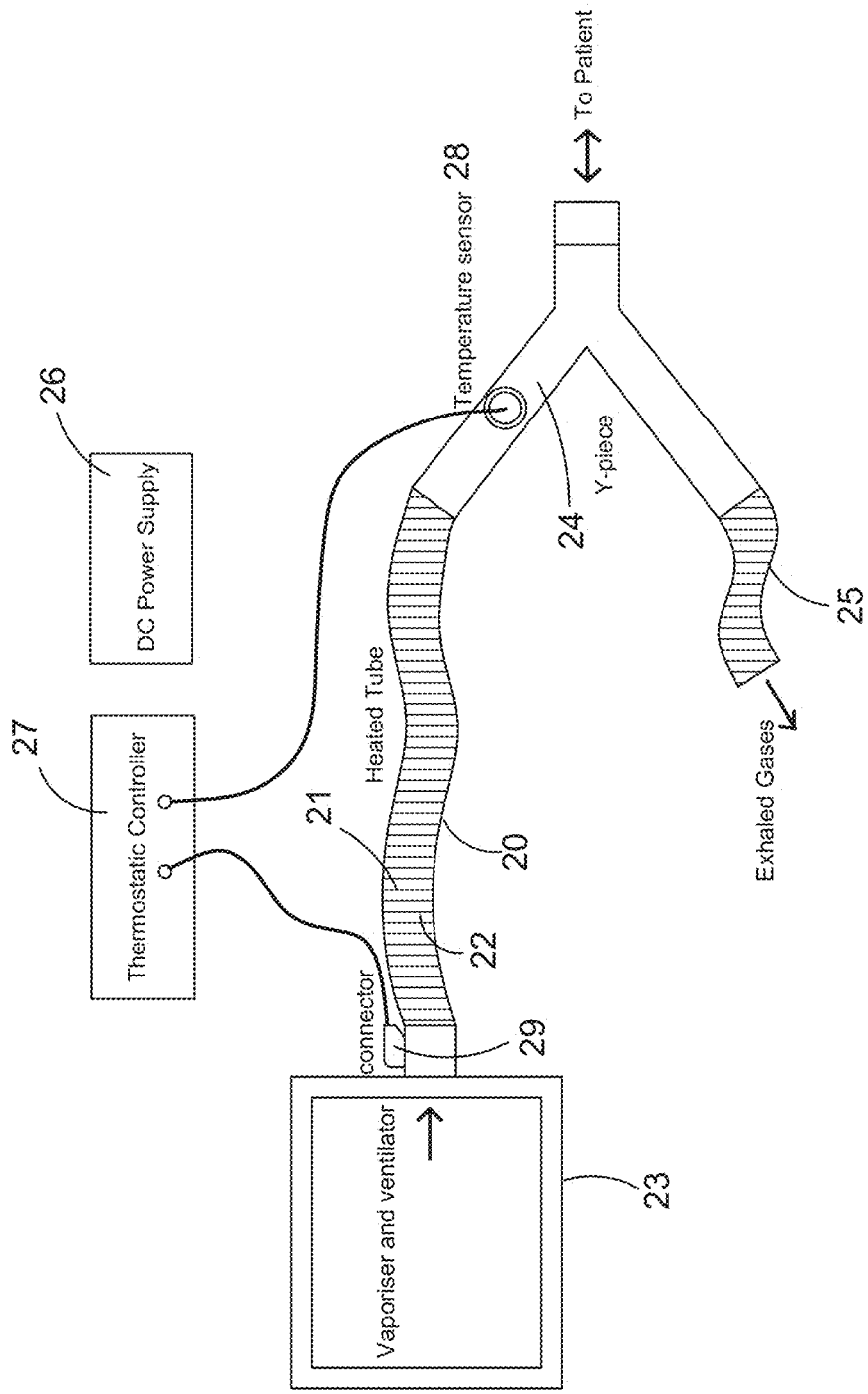
FIG. 2 is a diagram of part of an anaesthetic apparatus in accordance with an embodiment of the present invention.

An embodiment of the present invention is illustrated diagrammatically in FIG. 2. In this embodiment, the temperature of the patient is maintained (or at least temperature loss is minimised) in order to reduce the chances of hypothermia, by heating inspired gas. In this embodiment, inspired gas is heated in an anaesthetic delivery apparatus, during anaesthesia.

FIG. 2 schematically shows part of an anaesthetic circuit. In this embodiment, the circuit is a re-breathing circuit and is similar to the prior art circuit illustrated in FIG. 1, but also including a conduit 20 as inspired limb of the anaesthetic apparatus 1 and comprising a heating arrangement 21. In this embodiment, the heating arrangement 21 is a heating conductor running within the conduit 20. The conduit 20, in this embodiment, is a heated flexible hose.

In more detail, gas from the anaesthetic circuit (e.g. vaporiser and ventilator arrangement 22) enters a passageway 22 of the heated tube 20, which acts as the inspired limb of the re-breathing circuit, and is heated as it passes along the passageways 22. The heated gas enters a 'Y' piece 24 and is transmitted to the patient (who may be intubated or via a mask or some other delivery arrangement).

Exhaled gases travel via the expired limb 25 back into the anaesthetic circuit.

In this embodiment the expired limb 25 is not heated. Heating the gas in the inspired limb is sufficient to maintain the temperature of the patient. In other embodiments, however, the expired limb 25 may also include a heating arrangement to heat the expired gases to maintain temperature within the circuit, if required.

This embodiment is a closed circuit re-breathing system. An alternative embodiment may comprise a non-re-breathing open circuit, the inspired limb still being heated.

A DC power supply 26 is provided for the heating element 22 and a thermostatic controller 27 is provided to control operation of the power supply. A temperatures sensor 28, placed at the 'Y' piece 24 at the patient end of the heated tube 20 provides feedback to the thermostatic controller 27. A connector 29 connects to the heating element 22 to provide power.

The temperature sensor 28 extends in the 'Y' piece with its sensitive area in the inhalation gas flow. This sensor may typically be a thermistor, thermocouple, RTD or other suitable sensor to provide an different signal to the thermostatic controller 27.

The thermostatic controller 27 is provided with power by a mains DC power supply 26 or battery. The thermostatic controller 27 typically functions as an "ON-OFF" device switching about set point temperature with hysteresis or in a proportional mode (e.g. PRD). The thermostatic controller 27 may also provide a visual indication of the temperature (display).

This embodiment uses a microprocessor thermostat which discloses a "heat off" status as well as detecting if the temperature sensor is damaged or unplugged. This shuts down the tube heating protecting the patient from overheating. The device also has a data link (not shown) to a computer giving provision for reporting the current inhaled gas temperature and reporting heating state "ON-OFF", for example every 10 seconds (or other desired period). This data can be recorded by the computer.

Figure 12:
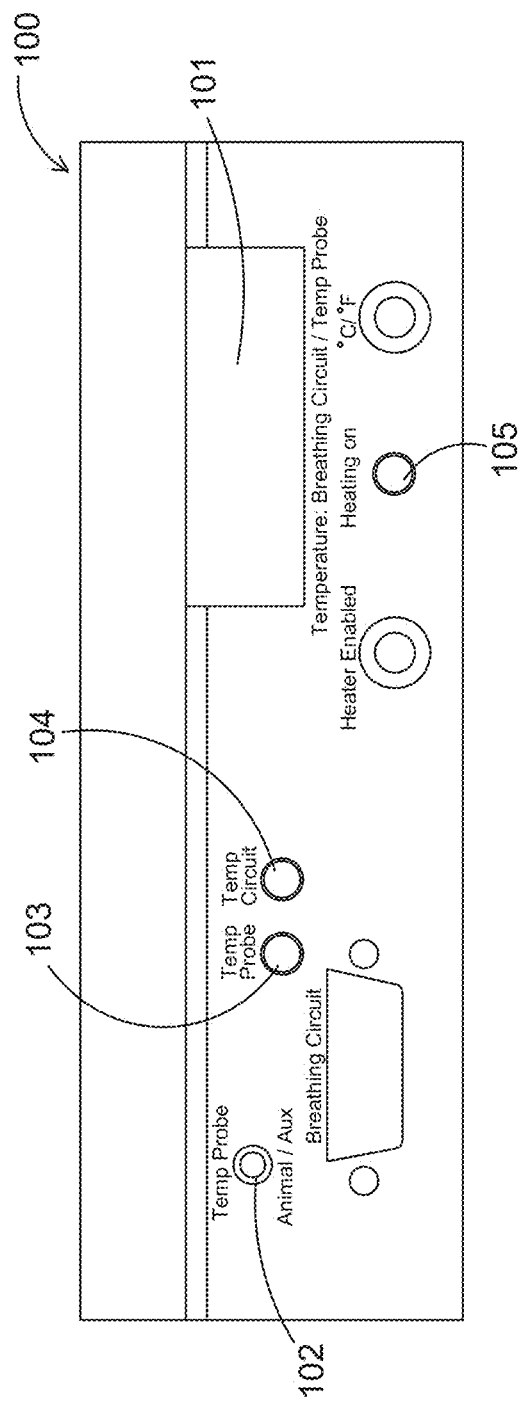
FIG. 12 is a front view of a control panel for an apparatus such as shown and described with reference to FIGS. 2-11.

FIG. 12 illustrates a controller in accordance with an embodiment of the present invention for controlling the tube heating. The controller 100 comprises a display 101 for displaying current temperature of the breathing circuit or the animal. An auxiliary temperature probe port 102 is provided to receive input from a temperature probe monitoring the actual bodily temperature of the patient. For example, the temperature probe could be a rectal or oesophageal thermometer monitoring the actual bodily temperature of the patient. Indicators "temp probe" 103 and "temp circuit" 104 indicate which temperature is being displayed by display 101 at any particular time. The display 101 may alternate displays between the probe temperature and the temperature of the anaesthetic circuit. The temperature of the circuit is monitored by a temperature sensor within one of the conduits (usually the expired limb) of the anaesthetic circuit, as discussed above.

Indicator light 105 indicates that heating is on. The controller 100 is arranged to control the heating depending on settings and also depending on feedback from the temperature probe and the temperature sensor in the circuit.

Monitoring the animal's actual temperature can facilitate regulation of the heating to be applied to the conduit. Measurement of the animal's actual temperature and the temperature of the expired limb of the anaesthetic circuit can be used to monitor the heat transfer of the patient.

In an embodiment the temperature sensor sensing the temperature near the breathing orifice of the patient (e.g. in the expired limb of an anaesthetic circuit) is relatively fast in response time so that it varies as the animal breathes. This can be used in embodiments to determine the respiratory rate of the patient.

The controller 100 has a connector such as a USB port to enable data on temperature (and any other data available) to be downloaded to a computing device.

In an embodiment, where the apparatus is implemented in an anaesthetic circuit, an inspired air/limb temperature sensor may also be included, so that the differential between the inspired, the expired temperature and, if required also the actual temperature of the animal, may be monitored. This can be important for research as well as other applications.

The temperature to which the gas is heated and the volume of the gas being provided to the patient will depend upon the patient. In this embodiment, the heating arrangement allows heating of inspired gas to be between 35-45° C. Warming inspired air is the sole source of heating for, for example, small dogs and cats, reduces heat loss and results in body temperatures of between 35-36° C. Heating to 40° C. will stop animals' temperatures dropping so no additional heating may be required in the circuit.

One of the problems with heating gas passing within a passageway within a tube is that the gas may not be heated sufficiently. Typical human anaesthetic circuits use 20 mm or 22 mm tubing. We have found that using this width of tubing may mean that the gas may not heat sufficiently. Further, typical tubing is corrugated. This can lead to turbulent flows, higher resistance and further difficulties in delivering heated gas. In the present embodiment, the tubing is reduced in diameter (to between 10-18 mm, preferably between 12-16 mm). In one embodiment the tubing used is 12 mm diameter (bore) and in another embodiment 16 mm (e.g. for larger patients).

Using lower diameter tubing is counter-intuitive, as it would be considered that this would provide a resistance to breathing that may be difficult for the patient under anaesthetic to overcome (particularly small animals). By providing smooth walled tubing which allows a laminar flow of gas along the tubing, this problem has been avoided. Low bore tubings, which allow for sufficient heating of the gas but still do not have great resistance to flow of gas to a patient, are therefore utilised in this embodiment.

Note that it is known in ventilation therapy, such as CPAP, to heat tubing in an expired limb in order to prevent "rainout" (condensation within the tubing). Heating in these systems is to 32° C. (which would be insufficient to prevent hypothermia and would be ineffective anyway because it would be in the expired pathway). Further, the heating in CPAP and the like systems is to heat the tube so that water does not condense on the walls. In the present invention, the heating arrangement is arranged to heat the gas passing within the tube passageways.

Figure 3:
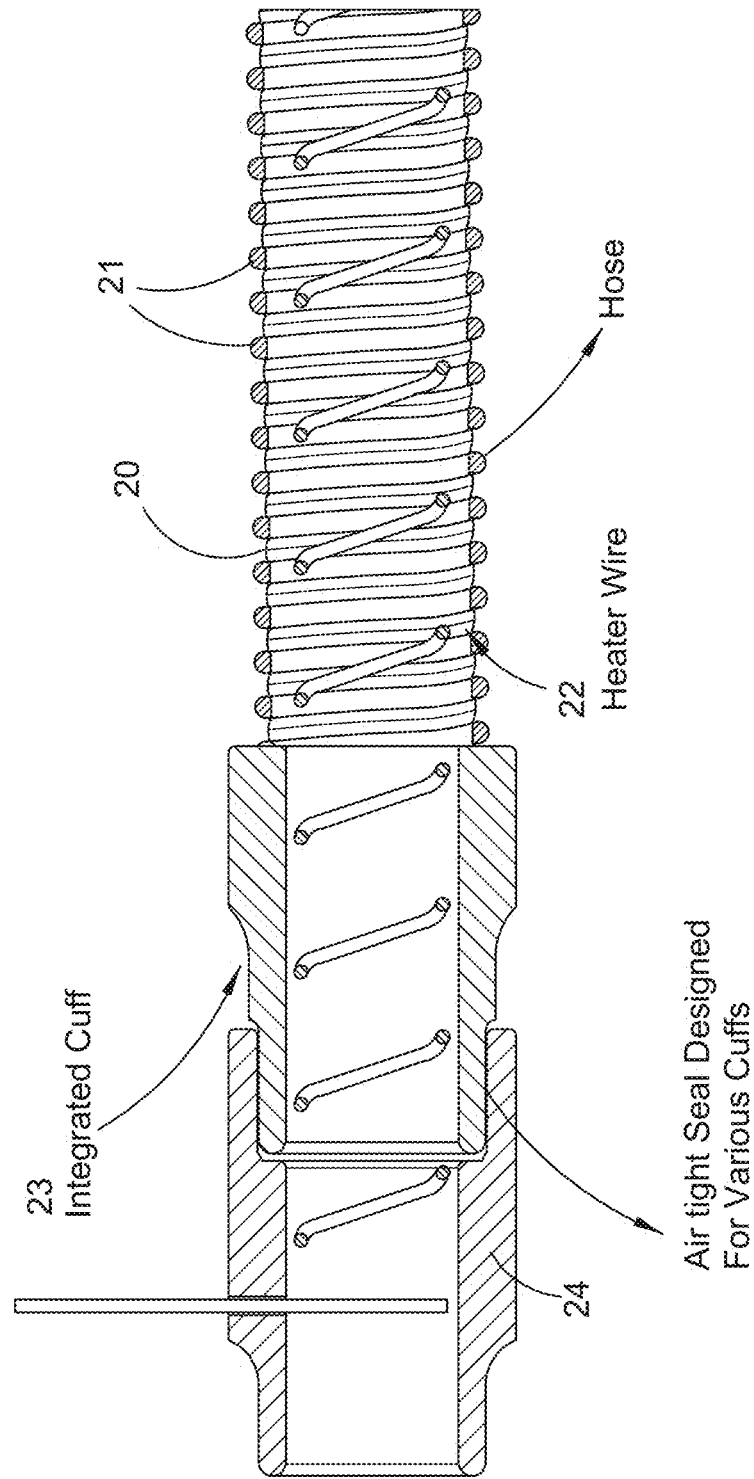
FIG. 3 is a sectional view of a conduit and heating arrangement in accordance with an embodiment of the present invention.
Figure 4:
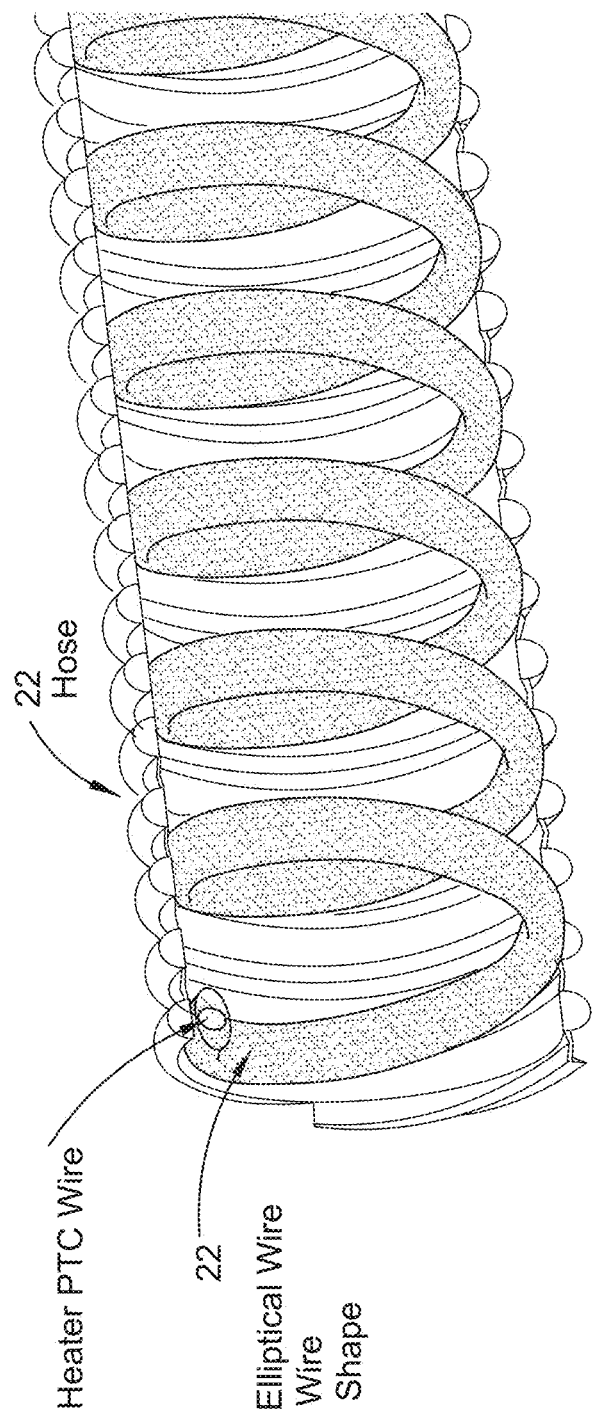
FIG. 4 is an exploded view of a conduit and heating arrangement in accordance with an embodiment of the present invention.

FIGS. 3 and 4 show cross-sections and exploded views of heated tubing in accordance with embodiments of the present invention. Referring to FIG. 3, the heated tubing 20 includes a plurality of external ribs 21 and a heating arrangement in the form of a coiled heating element 22. Also note there is an integrated cuff 23 that is used to connect to other elements 24 of the anaesthetic circuit. The integrated cuff 23 may be coloured so that the user can tell which tubing is the heated tubing and which end they should connect to the 'Y' piece 24.

FIG. 4 shows the arrangement in more detail, the heating element 22 is elliptical in cross-section and allows the heater arrangement to be torqued against the inside wall surface of the hose 22. This allows improved heat dispersion into the wall of the hose through greater contact air (note the wall of the hose contacts the gas flowing through the hose and therefore heats the gas). It also has improved aerodynamics with profiled shape and location against the tube wall.

Figure 5:
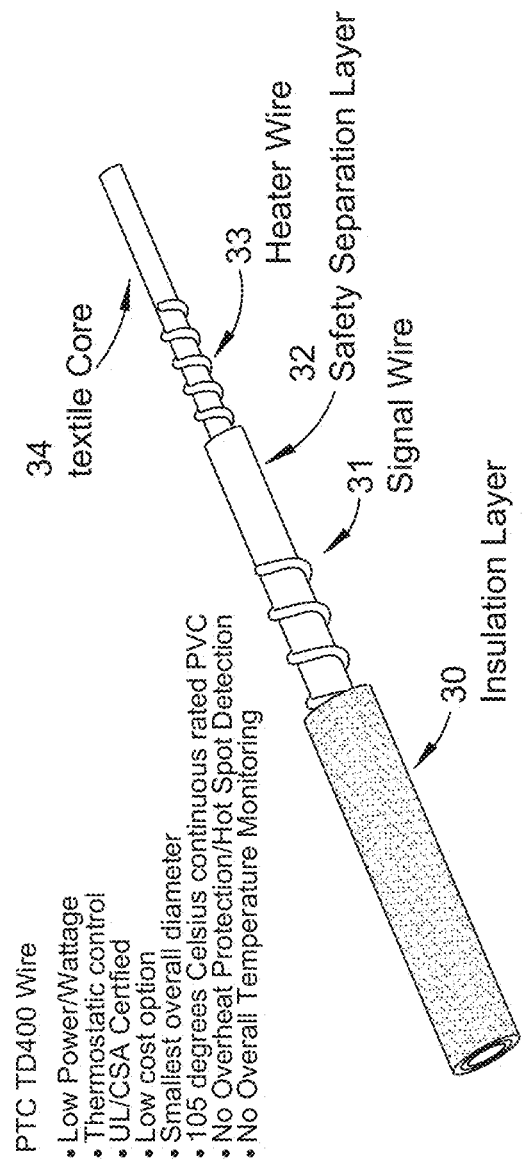
FIG. 5 is a diagram of a heating element for a heating arrangement in accordance with an embodiment of the present invention.

FIG. 5 shows an exploded view of the heating element, which comprises an insulation layer 30 passing around the element. In this embodiment, the heater wire is PTC TD400 wire. It includes a signal wire 31, along which data (e.g. temperature data) may be passed. It also includes a safety separation layer 32 and the heater wire 33. There is a textile core 34.

Note that other heating wire may be used in other embodiments and the invention is not limited to the PTC TD400 element.

Figure 6:
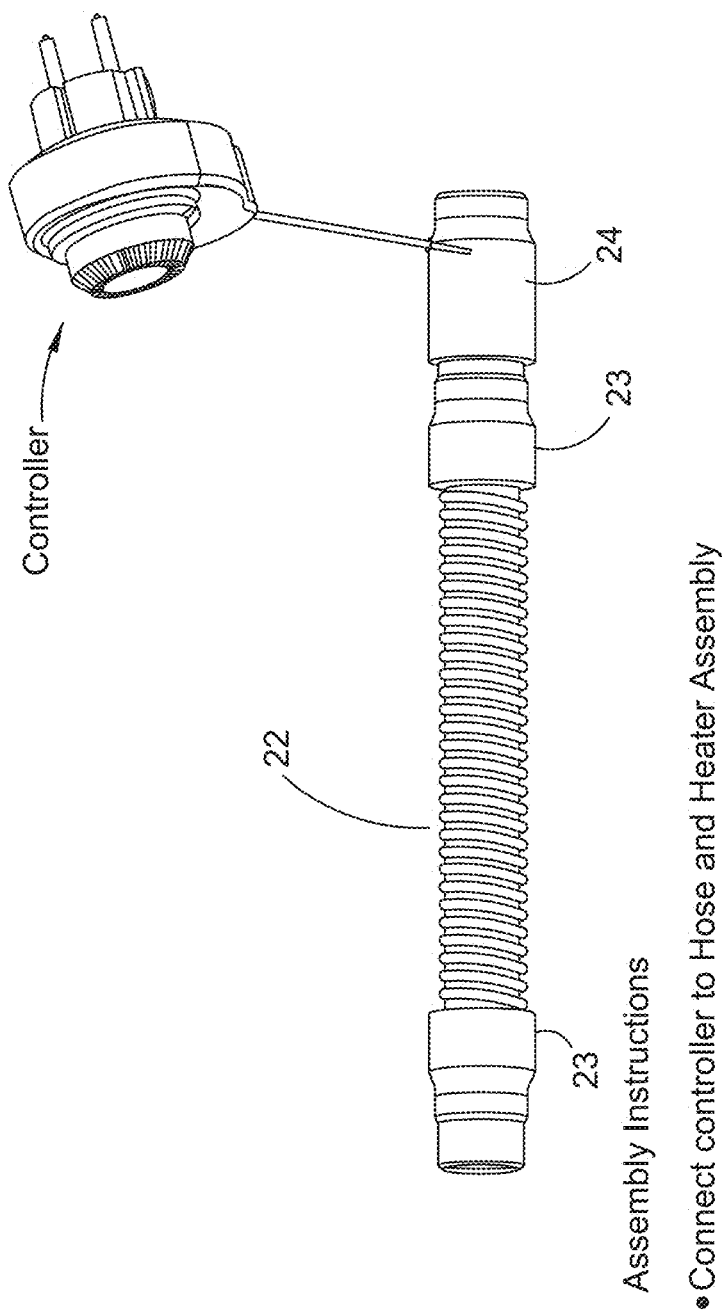
FIG. 6 shows a conduit and heating arrangement in accordance with an embodiment of the present invention.

FIG. 6 shows a complete hose 22 with end pieces 23 and 24 attached to a controller 27 which may be plugged into a power supply.

FIGS. 7A through 7D, show various views of heated tubing which may be used in embodiments of the present invention. End pieces 50 of the tubing 51 may be adapted to connect to standard fittings in anaesthetic circuits (e.g. 22 mm), whereas the tubing bore 52 may be of different diameter (e.g. 16 mm, 12 mm or other diameter).

Figure 8B:
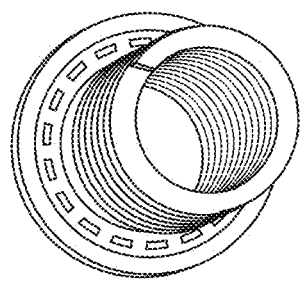
FIGS. 8A to 8E are perspective views of embodiments of heated tubing in accordance with the present invention.
Figure 8A:
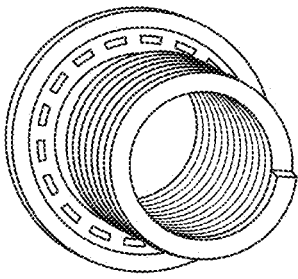
Figure 8C:
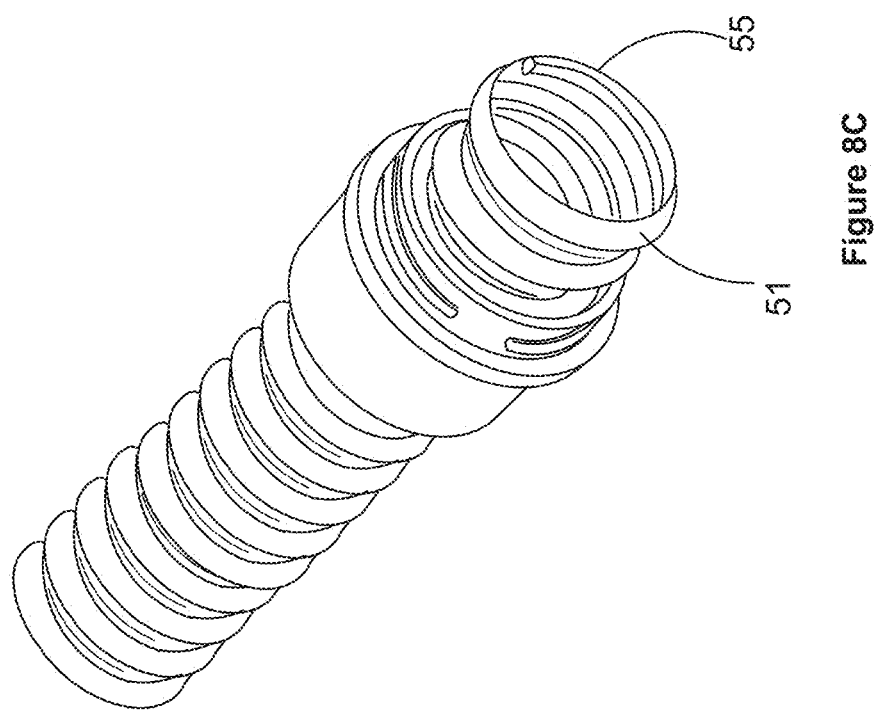

FIGS. 8A, 8B and 8C are representations of example tubing. It will be seen that the tubing is transparent, and that the heating wire passes underneath the ribs (see in particular FIG. 8C, showing the heating wire 55 passing under the ribs 51).

hose. Shown below in the table is the Comparative Breathing Hose Resistance which has not been adjusted for length or for the restriction size from 22 mm. Included in the results in the last column are resistance values of a standard 22 13 mm ID restriction described in the method.

| COMPARATIVE BREATHING HOSE RESISTANCE (NON ADJUSTED FOR LENGTH) | | | | | | | | |
|---|---|---|---|---|---|---|---|---|
| Flow Rate (L/min) | 12 mm Heated | 16 mm Heated | Pastiflex: 20 mm Heated | 22 mm Clear Cor. | 15 mm Clear Cor. Pediatric | Universal: F- Inspiratory | Universal: F- Expiratory | 22-13 mm Orifice |
| 10 | 0.12 | 0.05 | 0.02 | 0.01 | 0.08 | 0.09 | 0.14 | 0.02 |
| 20 | 0.31 | 0.08 | 0.01 | 0.00 | 0.25 | 0.28 | 0.39 | 0.02 |
| 30 | 0.83 | 0.21 | 0.05 | 0.01 | 0.63 | 0.68 | 0.85 | 0.08 |
| 40 | 1.62 | 0.42 | 0.10 | 0.03 | 1.17 | 1.28 | 1.49 | 0.17 |
| 50 | 2.89 | 0.72 | 0.22 | 0.10 | 2.07 | 2.14 | 2.62 | 0.29 |

Figure 8E:
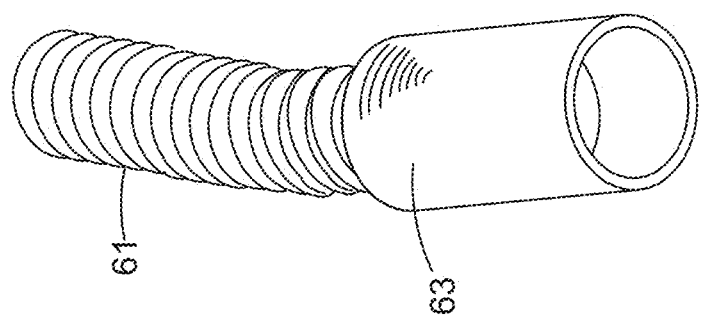
Figure 8D:
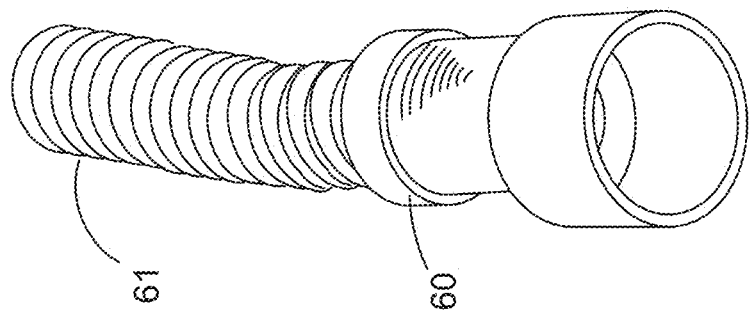

Referring to FIG. 8D, this shows a novel hard plastic moulded connector 60 attached to tubing in accordance with an embodiment of the invention 61. The connector is arranged to connect to a standard 22 mm anaesthesia machine.

FIG. 8E shows a soft rubber connector 63.

FIG. 9 shows an example of 12 mm tubing (the red tagged connectors are for the heated tubing and the non-coloured connectors are to the expired limb of the tubing). Similarly, FIG. 10 shows an example of 16 mm tubing.

FIG. 11 shows an electrical connector 70 being connected to heated tubing examples 71.

The smooth walled tubing as discussed above, promotes laminar flow (not turbulent) so is low resistance. This means that lower diameters can be used than with conventional anaesthetic circuits.

In an example embodiment, animals' temperature at the end of 1-3 hour anaesthesia for ophthalmology surgery using heated tubing (typically heats to 38-42° C. with 24 volt DC power supply) is around 35.5-38° C. with airway heating alone. Otherwise it would be between 32-35° C. or they would need a warm air heating blanket.

12 mm ID tube×1.5 m long—volume 170 ml:
Non-heated weight 58 gm
Heated weight 68 gm
15 mm ID tube×1.5 m long—volume 300 ml:
Non-heated weight 72 gm
Heated weight 74 gm In embodiments, a humidifier can be added to the anaesthetic system to humidify the gas.

In re-breathing circuits, the absorbance of carbon dioxide sodalime is exothermic with and gives off water. This can be used to keep the gas humidified.

The following examples give test results for resistance of various different types of hoses, including the 12 mm and 16 mm hoses in accordance with embodiments of the present invention.

EXAMPLE

All hoses were tested as they were produced, connected to standard anaesthetic machine 22 mm Tapered outlets identical to ones found on all soda lime absorbers near the one-way valves.

10-50 L/min air was delivered from a calibrated flowmeter and passed through the hose while it was flat and straight ensuring no pressure variances due to gravity or a coiled For the tested hoses, approximations were made for the restriction resistance and will be taken from the above table. The far right column shows the pressure drop for a standard 22-13 mm Orifice like those found in smaller hoses. After the restrictions were accounted for, approximations were made for resistance in the breathing hoses per meter. Each individual hose's test data and adjusted data are shown in the following tables. The hose at the top of each Table and final resistance/meter value are shown in the far right column.

This adjusted (indexed) data enabled us to make an approximate comparison on the efficiency of each hose design. Based on clinical experience and work from other researchers, we consider resistance of less than 0.5 cm $H_2O$ to be of negligible importance.

Figure 13:
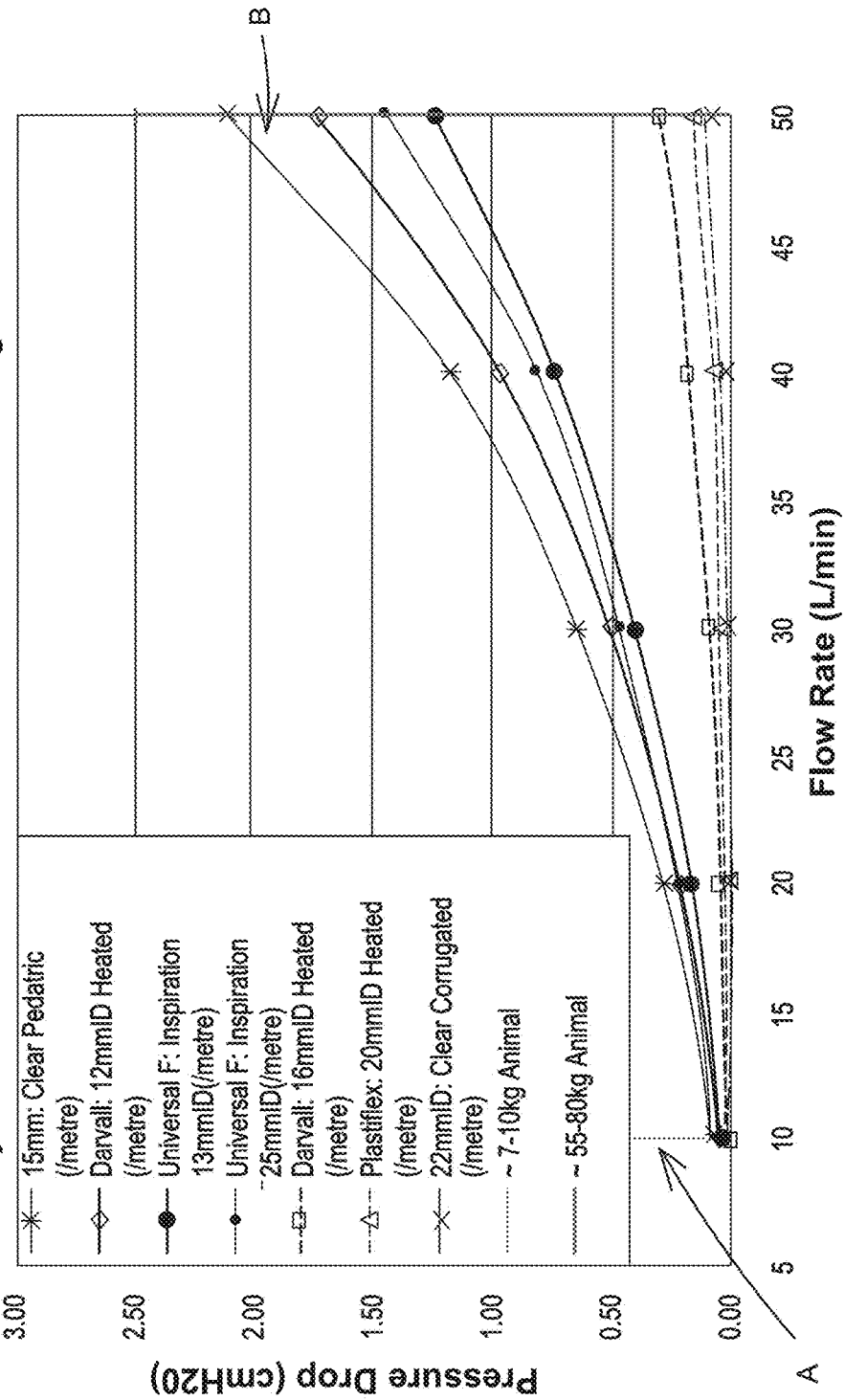
FIG. 13 is a graph which shows results of resistance to airflow, adjusted for connection restrictions and standardized for length (per meter).

FIG. 13 shows results of resistance to airflow, adjusted for connection restrictions and standardized for length (per meter). Airflows were tested from 10-50 L/min (which covers an animal range of ~7.5-10 kg (vertical line 'A') up to ~55-80 kg (vertical line 'B').

12 mm hose embodiment has less resistance than traditional corrugated 15 mm ID hose (known as "paediatric" breathing hose) and similar resistance to the expiratory limb (inside hose) of a Universal "F" circuit at flows less than 25 L/min (equivalent to a 20-30 kg dog's breath).

16 mm hose embodiment has similar resistance to Plastiflex 20 mm ID smooth wall hose and similar resistance to standard corrugated 22 mm ID hose at flows up to 50 L/min (equivalent to a breath from a 55-80 kg dog).

Test results for individual hoses are shown in the tables below. The far right column shows the data adjusted for hose connections and length.

TABLE HT-2

12 mm ID Adjusted Data
12 mm ID HEATED HOSE-1.5M LENGTH

| | 22-12 mm | | | | |
|---|---|---|---|---|---|
| Orrifice Restriction Flow L/min | Pressure Drop Total Circuit Limb cmH$_2$O | Pressure Drop (Approx) Inlet Orrifice cmH$_2$O | Pressure Drop Hose (Total) cmH$_2$O | Length Hose m | Pressure Drop Hose/ Meter cmH$_2$O |
| 10 | 0.12 | 0.02 | 0.11 | 1.5 | 0.07 |
| 20 | 0.31 | 0.02 | 0.30 | 1.5 | 0.20 |
| 30 | 0.83 | 0.08 | 0.74 | 1.5 | 0.50 |

TABLE HT-2-continued 12 mm ID Adjusted Data
12 mm ID HEATED HOSE-1.5M LENGTH 22-12 mm

| Orrifice Restriction Flow L/min | Pressure Drop Total Circuit Limb cmH$_2$O | Pressure Drop (Approx) Inlet Orrifice cmH$_2$O | Pressure Drop Hose (Total) cmH$_2$O | Length Hose m | Pressure Drop Hose/ Meter cmH$_2$O |
|---|---|---|---|---|---|
| 40 | 1.62 | 0.17 | 1.45 | 1.5 | 0.97 |
| 50 | 2.89 | 0.29 | 2.60 | 1.5 | 1.73 |

TABLE HT-3

16 mm ID Adjusted Data
16 mm ID HEATED HOSE-1.5M LENGTH 22-14 mm

| Orrifice Restriction Flow L/min | Pressure Drop Total Circuit Limb cmH$_2$O | Pressure Drop (Approx) Inlet Orrifice cmH$_2$O | Pressure Drop Hose (Total) cmH$_2$O | Length Hose m | Pressure Drop Hose/ Meter cmH$_2$O |
|---|---|---|---|---|---|
| 10 | 0.05 | 0.02 | 0.03 | 1.5 | 0.02 |
| 20 | 0.08 | 0.02 | 0.07 | 1.5 | 0.04 |
| 30 | 0.21 | 0.08 | 0.13 | 1.5 | 0.09 |
| 40 | 0.42 | 0.17 | 0.26 | 1.5 | 0.17 |
| 50 | 0.72 | 0.29 | 0.43 | 1.5 | 0.29 |

TABLE HT-4

Plastiflex 20 mm ID Adjusted Data
PLASTIFLEX 20 mm ID HEATED
HOSE FOR HUMANS-1.5M LENGTH Negligible

| Orrifice Restriction Flow L/min | Pressure Drop Total Circuit Limb cmH$_2$O | Pressure Drop (Approx) Inlet Orrifice cmH$_2$O | Pressure Drop Hose (Total) cmH$_2$O | Length Hose m | Pressure Drop Hose/ Meter cmH$_2$O |
|---|---|---|---|---|---|
| 10 | 0.02 | 0.00 | 0.02 | 1.5 | 0.01 |
| 20 | 0.01 | 0.00 | 0.01 | 1.5 | 0.01 |
| 30 | 0.05 | 0.00 | 0.05 | 1.5 | 0.03 |
| 40 | 0.10 | 0.00 | 0.10 | 1.5 | 0.07 |
| 50 | 0.22 | 0.00 | 0.22 | 1.5 | 0.15 |

TABLE HT-5

Clear Corrugated 22 mm ID Adjusted Data
CLEAR CORRUGATED 22 mm ID
BREATHING HOSE-1.5M LENGTH Negligible

| Orrifice Restriction Flow L/min | Pressure Drop Total Circuit Limb cmH$_2$O | Pressure Drop (Approx) Inlet Orrifice cmH$_2$O | Pressure Drop Hose (Total) cmH$_2$O | Length Hose m | Pressure Drop Hose/ Meter cmH$_2$O |
|---|---|---|---|---|---|
| 10 | 0.01 | 0.00 | 0.01 | 1.05 | 0.01 |
| 20 | 0.00 | 0.00 | 0.00 | 1.05 | 0.00 |
| 30 | 0.01 | 0.00 | 0.01 | 1.05 | 0.01 |
| 40 | 0.03 | 0.00 | 0.03 | 1.05 | 0.03 |
| 50 | 0.10 | 0.00 | 0.10 | 1.05 | 0.10 |

TABLE HT-6

Clear Corrugated 15 mm ID Paediatric Adjusted Data
CLEAR CORRUGATED 15 mm ID
PEDIATRIC BREATHING HOSE-0.85M LENGTH 22-13 mm

| Orrifice Restriction Flow L/min | Pressure Drop Total Circuit Limb cmH$_2$O | Pressure Drop (Approx) Inlet Orrifice cmH$_2$O | Pressure Drop Hose (Total) cmH$_2$O | Length Hose m | Pressure Drop Hose/ Meter cmH$_2$O |
|---|---|---|---|---|---|
| 10 | 0.08 | 0.02 | 0.06 | 0.85 | 0.07 |
| 20 | 0.25 | 0.02 | 0.23 | 0.85 | 0.28 |
| 30 | 0.63 | 0.08 | 0.55 | 0.85 | 0.64 |
| 40 | 1.17 | 0.17 | 1.00 | 0.85 | 1.18 |
| 50 | 2.07 | 0.29 | 1.79 | 0.85 | 2.10 |

TABLE HT-7

F-Inspiratory 13 mm ID Adjusted Data
KING SYSTEMS UNIVERSAL F CIRCUIT
INSPIRITORY ARM-1.5M LENGTH 22-13 mm

| Orrifice Restriction Flow L/min | Pressure Drop Total Circuit Limb cmH$_2$O | Pressure Drop (Approx) Inlet Orrifice cmH$_2$O | Pressure Drop Hose (Total) cmH$_2$O | Length Hose m | Pressure Drop Hose/ Meter cmH$_2$O |
|---|---|---|---|---|---|
| 10 | 0.09 | 0.02 | 0.07 | 1.5 | 0.05 |
| 20 | 0.28 | 0.02 | 0.26 | 1.5 | 0.17 |
| 30 | 0.68 | 0.08 | 0.60 | 1.5 | 0.40 |
| 40 | 1.28 | 0.17 | 1.11 | 1.5 | 0.74 |
| 50 | 2.14 | 0.29 | 1.86 | 1.5 | 1.24 |

TABLE HT-8

F-Expiratory 25 mm ID Adjusted Data
KING SYSTEMS UNIVERSAL F CIRCUIT
EXPIRATORY ARM-1.8M LENGTH Negligible

| Orrifice Restriction Flow L/min | Pressure Drop Total Circuit Limb cmH$_2$O | Pressure Drop (Approx) Inlet Orrifice cmH$_2$O | Pressure Drop Hose (Total) cmH$_2$O | Length Hose m | Pressure Drop Hose/ Meter cmH$_2$O |
|---|---|---|---|---|---|
| 10 | 0.14 | 0.00 | 0.14 | 1.8 | 0.08 |
| 20 | 0.39 | 0.00 | 0.39 | 1.8 | 0.22 |
| 30 | 0.85 | 0.00 | 0.85 | 1.8 | 0.47 |
| 40 | 1.49 | 0.00 | 1.49 | 1.8 | 0.83 |
| 50 | 2.62 | 0.00 | 2.62 | 1.8 | 1.45 |

In the above embodiments, heating is applied to the conduit by the heating apparatus in the form of a heating element. In an alternative embodiment, heating may be applied to the conduit in other ways. For example, heating may be applied externally, for example by passing the conduit through a warming device e.g. a water bath, or an electrical bath. In another embodiment, the conduit may be heated by a blanket which is in turn being used to maintain the warmth of the patient. Heating blankets for use during recovery and surgery are known. They may use warm air passing through the blanket to maintain the heat of the patient. Such heating blankets are disclosed in the Applicant's earlier patent applications PCT/AU2003/001626, PCT/AU2007/001553, PCT/AU2010/000383 and PCT/

AU2011/000410. In an embodiment, the conduit may be placed contiguous with a surface of the heating blanket, in order to heat the conduit and therefore the air within the conduit. In this case, the tubing would not necessarily need a heating element in order to provide the same advantages of heating the air, as discussed above.

In the above embodiment an anaesthetic apparatus for keeping a patient warm is disclosed. The invention is not limited to an anaesthetic apparatus. In alternative embodiments, for example, a warmed hose could be used on an inspiration tubing to warm air (or other gas) being breathed by a patient in recovery.

In the above embodiments, the apparatus utilises heated tubing which may be circular in diameter. The invention is not limited to circular tubing. The cross-section of the tubing may be other shapes such as elliptical.

While the above described embodiments of the invention are particularly suitable for maintaining heat of small patients during medical procedures, the invention is not limited to this. The invention may be used with larger patients including human adults.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The claims defining the invention are as follows:

1. An anaesthetic apparatus arranged for the delivery of anaesthesia to a patient, the apparatus comprising:
    a conduit for delivering a gas including anaesthetic to a patient, wherein the conduit comprises a heating arrangement arranged to heat the gas within the conduit,
    a first temperature sensor arranged to sense temperature of the gas at a breathing orifice of a patient when a patient is connected to the apparatus,
    a second temperature sensor arranged to sense the actual bodily temperature of the patient, and
    a controller arranged to receive from the first temperature sensor the sensed temperature of the gas at the breathing orifice of the patient and receive from the second temperature sensor the sensed temperature of the patient, the controller being configured to regulate the heating arrangement for heating the gas to warm the patient to regulate the patient's temperature based on the sensed temperature of the gas and the sensed actual bodily temperature of the patient.

2. The anaesthetic apparatus in accordance with claim 1, wherein the heating arrangement is arranged to heat the gas to a temperature in a range between 30 and about 50° C.

3. The anaesthetic apparatus in accordance with claim 1, wherein the heating arrangement is arranged to heat the gas to a temperature in a range between 35 and about 45° C.

4. The anaesthetic apparatus in accordance with claim 1, wherein the heating arrangement is arranged to heat the gas to a temperature in a range between 35 and about 38° C.

5. The anaesthetic apparatus in accordance with claim 1, further comprising an inspired limb of the anaesthetic apparatus, wherein the inspired limb comprising the conduit.

6. The anaesthetic apparatus in accordance with claim 1, wherein the conduit further comprises tubing, wherein the tubing comprises a tubing wall defining a passageway along which gas may pass, and wherein the internal surface of the tubing wall is smooth.

7. The anaesthetic apparatus in accordance with claim 6, wherein the heating arrangement comprises a conductive heating element wound about the tubing wall.

8. The anaesthetic apparatus in accordance with claim 7, wherein the conductive heating element is wound about the internal surface of the tubing wall.

9. The anaesthetic apparatus in accordance with claim 6, wherein the passageway of the tubing is between about 10 and about 18 mm in diameter.

10. The anaesthetic apparatus in accordance with claim 6, wherein the passageway of the tubing is between about 12 and about 16 mm in diameter.

11. The anaesthetic apparatus in accordance with claim 1, wherein the controller is arranged to monitor heat transfer to a patient based on actual temperature of a patient and temperature of gas expired by the patient sensed by the first temperature sensor at the breathing orifice and the controller is arranged to further regulate the heating arrangement for heating the gas based on the heat transfer.

12. A method of maintaining the warmth of a patient during anaesthesia, the method comprising:
    a step of delivering warmed gas to the patient during the anaesthesia via a conduit comprising a heating arrangement arranged to heat the gas within the conduit,
    sensing temperature of the gas at a breathing orifice of a patient using a first temperature sensor,
    sensing the actual bodily temperature of the patient using a second temperature sensor,
    receiving by a controller from the first temperature sensor the sensed temperature of the gas at the breathing orifice of the patient and from the second temperature sensor the sensed temperature of the patient, and
    regulating the heating arrangement by the controller to heat the gas to warm the patient to regulate the patient's temperature based on the sensed temperature of the gas and the sensed actual bodily temperature of the patient.

13. An apparatus for maintaining patient warmth during a medical procedure, the apparatus comprising:
    a conduit along which gas is passed for breathing by the patient, wherein the conduit comprises a heating arrangement arranged to heat the gas within the conduit,
    a first temperature sensor arranged to sense temperature of the gas at a breathing orifice of a patient when a patient is connected to the apparatus,
    a second temperature sensor arranged to sense the actual bodily temperature of the patient, and
    a controller arranged to receive from the first temperature sensor the sensed temperature of the gas at the breathing orifice of the patient and receive from the second temperature sensor the sensed temperature of the patient, the controller being configured to regulate the heating arrangement for heating the gas to warm the patient to regulate the patient's temperature based on the sensed temperature of the gas and the sensed actual bodily temperature of the patient.

14. The apparatus in accordance with claim 13, wherein the controller is arranged to monitor heat transfer to a patient based on actual bodily temperature of a patient and temperature of gas expired by the patient sensed by the first temperature sensor at the breathing orifice and the controller is arranged to further regulate the heating arrangement for heating the gas based on the heat transfer.

15. The apparatus in accordance with claim 14, wherein the first temperature sensor is relatively fast in response time and the controller is further arranged to monitor respiratory rate based on fast variation in the temperature sensed by the first temperature sensor.

16. The anaesthetic apparatus in accordance with claim 11 wherein the first temperature sensor is relatively fast in response time and the controller is further arranged to monitor respiratory rate based on fast variation in the temperature sensed by the first temperature sensor.

17. The method in accordance with claim 12, further comprising the steps of:
- monitoring heat transfer to a patient by the controller based on actual bodily temperature of a patient and temperature of gas expired by the patient sensed by the first temperature sensor at the breathing orifice; and
- regulating the heating arrangement by the controller for heating the gas based on the heat transfer.

18. The method in accordance with claim 17, wherein the first temperature sensor is relatively fast in response time and further comprising monitoring respiratory rate by the controller based on fast variation in the temperature.

* * * * *